United States Patent
Kohr, II

(10) Patent No.: US 12,083,305 B1
(45) Date of Patent: Sep. 10, 2024

(54) DISPOSABLE PERSONAL TOWEL CLEANING KIT

(71) Applicant: James Kohr, II, Glen Rock, PA (US)

(72) Inventor: James Kohr, II, Glen Rock, PA (US)

(*) Notice: Subject to any disclaimer, the term of this patent is extended or adjusted under 35 U.S.C. 154(b) by 388 days.

(21) Appl. No.: 17/567,981

(22) Filed: Jan. 4, 2022

(51) Int. Cl.
*B65D 71/08* (2006.01)
*A47K 10/16* (2006.01)
*A61M 35/00* (2006.01)
*B65D 75/00* (2006.01)

(52) U.S. Cl.
CPC .......... *A61M 35/006* (2013.01); *A47K 10/16* (2013.01); *B65D 75/002* (2013.01); *A61M 2209/06* (2013.01)

(58) Field of Classification Search
CPC .............. B65D 75/002; A61M 35/006; A61M 2209/06; A47K 10/16
USPC ........ 206/205, 213, 363, 494, 497, 570, 581
See application file for complete search history.

(56) References Cited

U.S. PATENT DOCUMENTS

| | | | |
|---|---|---|---|
| 4,003,509 A | 1/1977 | Camarero | |
| 4,610,357 A * | 9/1986 | Nakamura | B65B 25/145 383/207 |
| 4,702,378 A * | 10/1987 | Finkel | A61F 15/00 206/581 |
| 5,082,707 A | 1/1992 | Fazio | |
| 5,322,918 A | 6/1994 | Kirby | |
| 5,464,096 A * | 11/1995 | Hurwitz | B08B 1/00 206/812 |
| 6,446,795 B1 * | 9/2002 | Allen | B65D 75/5855 206/812 |
| D578,309 S | 10/2008 | Johnston | |
| 9,603,781 B2 * | 3/2017 | Gomez | B65B 55/02 |
| 2003/0029740 A1 | 2/2003 | Caveness | |
| 2004/0109970 A1 | 6/2004 | Forsyth | |
| 2006/0151351 A1 * | 7/2006 | Hughes | B65D 81/3261 206/494 |
| 2014/0058981 A1 * | 2/2014 | Mastromarco | B32B 7/12 428/221 |

FOREIGN PATENT DOCUMENTS

CA      2824546      2/2014

\* cited by examiner

*Primary Examiner* — Luan K Bui
(74) *Attorney, Agent, or Firm* — Kyle A. Fletcher, Esq.

(57) ABSTRACT

The disposable personal towel cleaning kit is a kit. The disposable personal towel cleaning kit is a therapeutic apparatus. The disposable personal towel cleaning kit is adapted for use with a patient. The disposable personal towel cleaning kit cleans the patient. The disposable personal towel cleaning kit comprises a cleaning towel and a cosmetic media towel. The cleaning towel is intended for a single use. The cosmetic media towel is intended for a single use. The cleaning towel is disposable. The cosmetic media towel is disposable. The cleaning towel applies a cleaning solution to the skin of the patient. The cosmetic media towel applies a cosmetic media solution to the skin of the patient.

12 Claims, 3 Drawing Sheets

DISPOSABLE PERSONAL TOWEL CLEANING KIT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of towels. (A47K10/02)

SUMMARY OF INVENTION

The disposable personal towel cleaning kit is a kit. The disposable personal towel cleaning kit is a therapeutic apparatus. The disposable personal towel cleaning kit is adapted for use with a patient. The disposable personal towel cleaning kit cleans the patient. The disposable personal towel cleaning kit comprises a cleaning towel and a cosmetic media towel. The cleaning towel is intended for a single use. The cosmetic media towel is intended for a single use. The cleaning towel is disposable. The cosmetic media towel is disposable. The cleaning towel applies a cleaning solution to the skin of the patient. The cosmetic media towel applies a cosmetic media solution to the skin of the patient.

These together with additional objects, features and advantages of the disposable personal towel cleaning kit will be readily apparent to those of ordinary skill in the art upon reading the following detailed description of the presently preferred, but nonetheless illustrative, embodiments when taken in conjunction with the accompanying drawings.

In this respect, before explaining the current embodiments of the disposable personal towel cleaning kit in detail, it is to be understood that the disposable personal towel cleaning kit is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the disposable personal towel cleaning kit.

It is therefore important that the claims be regarded as including such equivalent construction insofar as they do not depart from the spirit and scope of the disposable personal towel cleaning kit. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
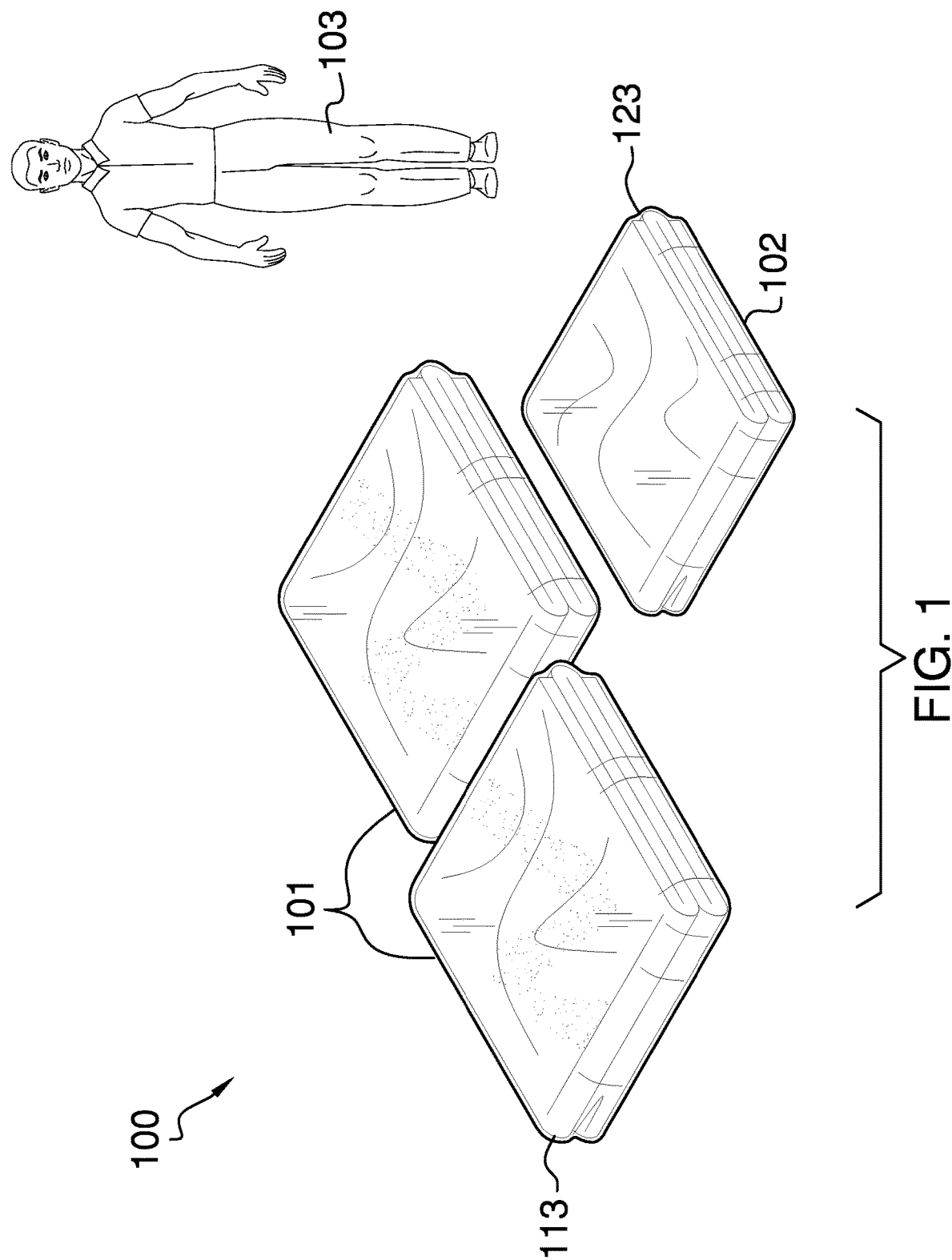
FIG. 1 is a perspective view of an embodiment of the disclosure.
Figure 2:
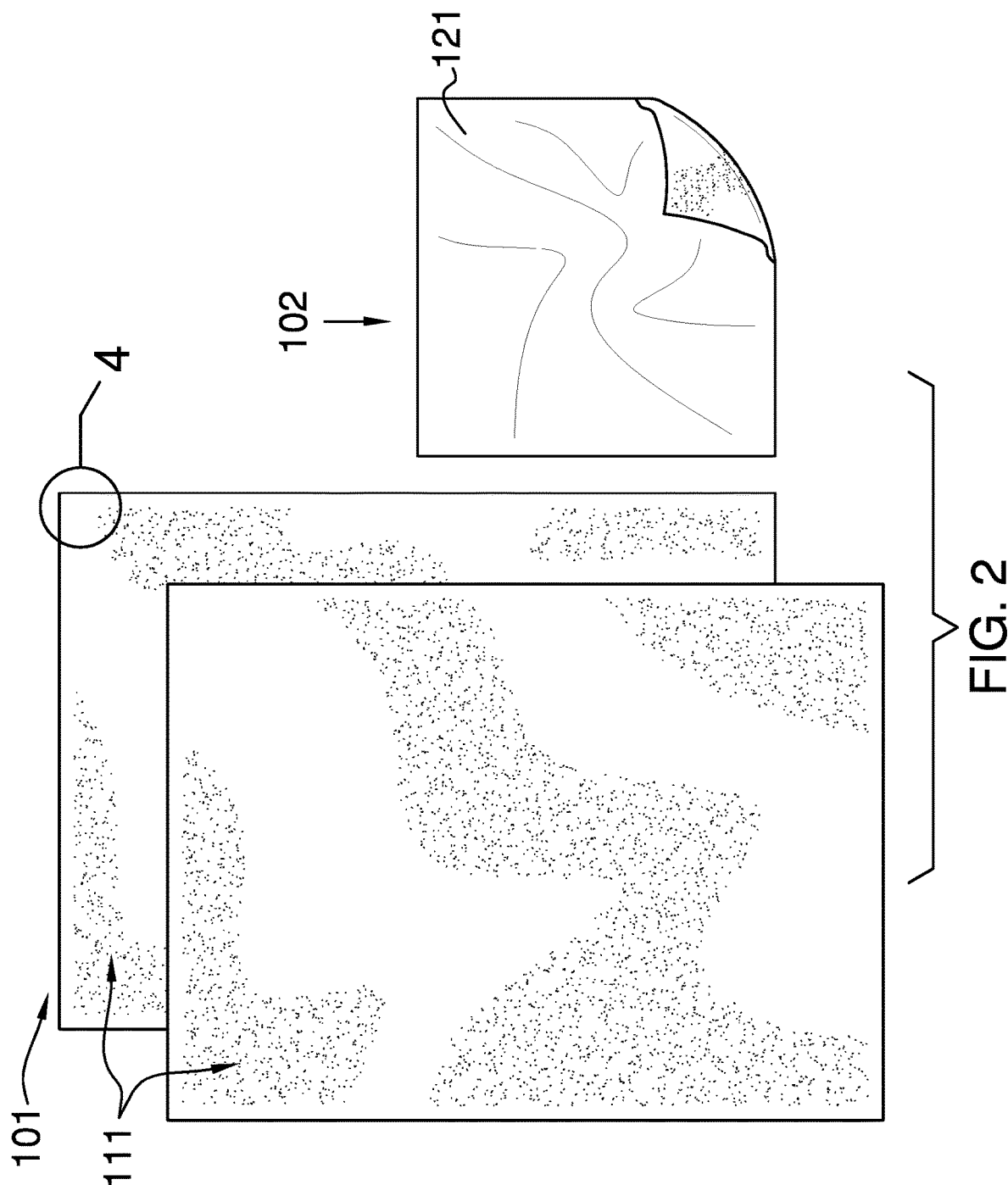
FIG. 2 is a front view of an embodiment of the disclosure.
Figure 3:
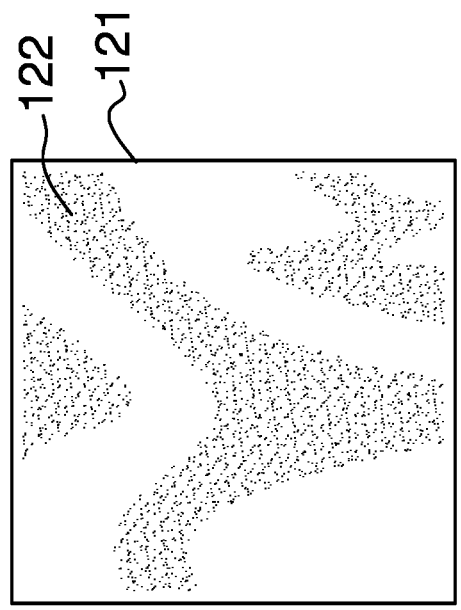
FIG. 3 is a detail view of an embodiment of the disclosure.
Figure 4:
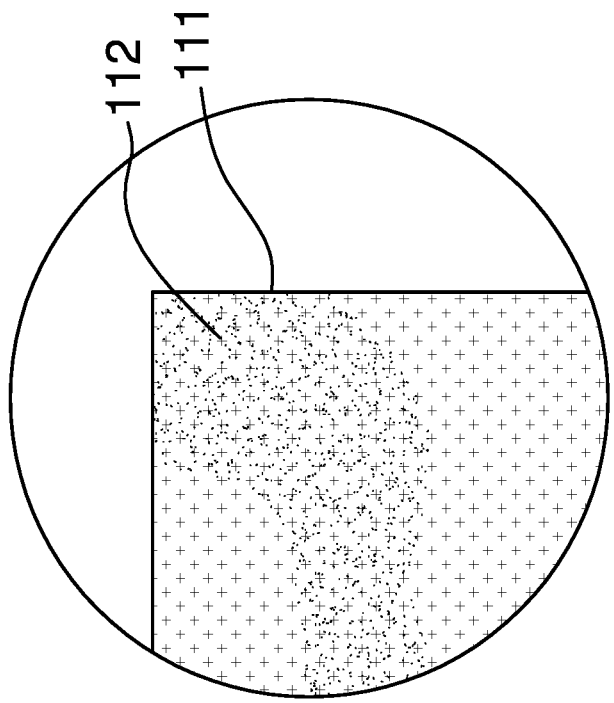
FIG. 4 is a detail view of an embodiment of the disclosure.

Detailed reference will now be made to one or more potential embodiments of the disclosure, which are illustrated in FIGS. 1 through 4.

The disposable personal towel cleaning kit 100 (hereinafter invention) is a kit. The invention 100 is a therapeutic apparatus. The invention 100 is adapted for use with a patient 103. The invention 100 cleans the patient 103. The invention 100 comprises a cleaning towel 101 and a cosmetic media towel 102. The cleaning towel 101 is intended for a single use. The cosmetic media towel 102 is intended for a single use. The cleaning towel 101 is disposable. The cosmetic media towel 102 is disposable. The cleaning towel 101 applies a cleaning solution 112 to the skin of the patient 103. The cosmetic media towel 102 applies a cosmetic media solution 122 to the skin of the patient 103.

The patient 103 uses the cleaning towel 101 to apply the cleaning solution 112 to the skin of the patient 103 for therapeutic purposes. The patient 103 uses the cosmetic media towel 102 to apply the cosmetic media solution 122 to the skin of the patient 103 for therapeutic purposes. The patient 103 is defined elsewhere in this disclosure.

The cleaning towel 101 is a sheeting structure. The cleaning towel 101 is a flexible structure. The cleaning towel 101 is a textile based structure. The cleaning towel 101 is an absorbent structure. The cleaning towel 101 applies a cleaning solution 112 to the skin of the patient 103. The cleaning towel 101 is a disposable structure that is intended for a single use. The cleaning towel 101 comprises a first textile sheeting 111, a cleaning solution 112, and a first shrink wrap 113.

The first textile sheeting 111 is a sheeting structure. The first textile sheeting 111 is a flexible structure. The first textile sheeting 111 is a textile based structure. The first textile sheeting 111 is an absorbent structure. The first textile sheeting 111 is a disposable structure that is intended for a single use.

The cleaning solution 112 is a liquid phase chemical. The first textile sheeting 111 absorbs and stores the cleaning solution 112 in anticipation of use. The cleaning solution 112 is a phytochemical. The cleaning solution 112 is a surfactant. The cleaning solution 112 removes polar and non-polar molecular structures that are on the skin of the patient 103. The cleaning solution 112 dissolves polar and non-polar molecular structures that are on the skin of the patient 103. The friction generated by rubbing the first textile sheeting 111 against the skin of the patient 103 acts to further release the polar and non-polar molecular structures that are on the skin of the patient 103. The polar and non-polar molecular structures captured by the cleaning towel 101 are disposed of when the cleaning towel 101 is disposed of.

The first shrink wrap 113 is a plastic structure. The first shrink wrap 113 is a fluid impermeable structure. The first shrink wrap 113 is a disposable structure that is intended for a single use. The first shrink wrap 113 is a shrink wrap used to enclose the first textile sheeting 111 and the cleaning solution 112. The first shrink wrap 113 forms a fluid impermeable protected space around the first textile sheeting 111 and the cleaning solution 112. The first shrink wrap 113 is formed from a heat shrink material. The first shrink wrap 113 is heated to wrap tightly around the first textile sheeting 111 and the cleaning solution 112. The tight fit first shrink wrap 113 inhibits the evaporation of the cleaning solution 112 from the first textile sheeting 111 while the cleaning towel 101 is in storage.

The cosmetic media towel 102 is a sheeting structure. The cosmetic media towel 102 is a flexible structure. The cosmetic media towel 102 is a textile based structure. The cosmetic media towel 102 is an absorbent structure. The cosmetic media towel 102 applies a cosmetic media solution 122 to the skin of the patient 103. The cosmetic media towel 102 is a disposable structure that is intended for a single use. The cosmetic media towel 102 comprises a second textile sheeting 121, a cosmetic media solution 122, and a second shrink wrap 123.

The second textile sheeting 121 is a sheeting structure. The second textile sheeting 121 is a flexible structure. The second textile sheeting 121 is a textile based structure. The second textile sheeting 121 is an absorbent structure. The second textile sheeting 121 is a disposable structure that is intended for a single use.

The cosmetic media solution 122 is a liquid phase chemical. The second textile sheeting 121 absorbs and stores the cosmetic media solution 122. The cosmetic media solution 122 is a phytochemical. The cosmetic media solution 122 is a pharmacologically active media. The cosmetic media solution 122 provides a therapeutic benefit to the skin of the patient 103. The cosmetic media solution 122 is topically applied to the skin of the patient 103. The friction generated by rubbing the second textile sheeting 121 against the skin of the patient 103 acts to evenly apply the cosmetic media solution 122 to the skin of the patient 103. The cosmetic media solution 122 is disposed of when the cosmetic media towel 102 is disposed of.

The second shrink wrap 123 is a plastic structure. The second shrink wrap 123 is a fluid impermeable structure. The second shrink wrap 123 is a disposable structure that is intended for a single use. The second shrink wrap 123 is a shrink wrap used to enclose the second textile sheeting 121 and the cosmetic media solution 122. The second shrink wrap 123 forms a fluid impermeable protected space around the second textile sheeting 121 and the cosmetic media solution 122. The second shrink wrap 123 is formed from a heat shrink material. The second shrink wrap 123 is heated to wrap tightly around the second textile sheeting 121 and the cosmetic media solution 122. The tight fit second shrink wrap 123 inhibits the evaporation of the cosmetic media solution 122 from the second textile sheeting 121 while the cosmetic media towel 102 is in storage.

The following definitions were used in this disclosure:

Absorbent: As used in this disclosure, absorbent is an adjective that refers to a material that is able to soak up a liquid such as water.

Alkaloid: As used in this disclosure, an alkaloid refers to a chemical with a molecular structure that contains one or more heterocyclic rings. The alkaloid generally has a high pH (i.e., is a basic substance). An alkaloid is typically soluble in water with a low (acidic) pH and soluble in lipids with a neutral or high (basic) pH.

Barrier: As used in this disclosure, a barrier is a physical obstacle that forms a boundary between a first space and a second space. The barrier prevents the passage of an object between the first space and the second space.

Biological Alkaloid: As used in this disclosure, a biological alkaloid is a class of phytochemical. The biological alkaloid is identified as phytochemical that contains one or more alkaloid structures. The biological alkaloids are believed to provide benefits. Most biological alkaloids act as either a depressant (for example morphine (CAS 57-27-2)) or stimulant (for example caffeine (CAS 58-08-2)) to the nervous system. Biological alkaloids are also effective in disrupting the cellular membranes of microorganisms including evolved viruses.

Biological Thiol: As used in this disclosure, a biological thiol is a class of phytochemical. The biological thiol is identified as a thiol functional group that is attached to a phytochemical. In general, all biological thiols act as an antioxidant. The biological thiols include, but are not limited to, glutathione (CAS 70-18-8), N-Acetylcysteine (CAS 619-91-1; Abbreviated NAC), and captopril (CAS 62571-82-2). Glutathione (CAS 70-18-8) is a pharmacologically active media that believed to provide benefits: a) in metabolic regulation; and, b) as a chemical modulator in the neurotransmission process. N-Acetylcysteine (CAS 619-91-1) is a pharmacologically active media that believed to provide therapeutic benefits by breaking up accumulations of mucus in the lungs. There are preliminary findings that N-Acetylcysteine (CAS 619-91-1) may be an effective treatment for mild psychiatric disorders. Captopril (CAS 62571-82-2) is a pharmacologically active media that believed to provide benefits in the treatment of hypertension.

Chemical: As used in this disclosure, a chemical refers to a substance of a known or fixed composition. The term chemical is used to describe the substance when the details of the composition of the substance or properties of the substance are considered relevant to the disclosure at bar. The term properties is taken to mean both the measurable properties of the substance and the interactions of a first chemical with a second chemical. The term compound refers to: a) a chemical structure that comprises a one or more chemical bonds; or, b) a unified chemical structure formed from mixture of chemicals. The term compound is informally considered a synonym for the term chemical. The term chemistry refers to the study and the use of the knowledge of the composition and properties of chemicals. The terms chemical reaction refers to the interactions between two or more chemical structures.

Chemical Bond: As used in this disclosure, a chemical bond refers to an attractive force between a first molecule or atom and a second molecule or atom. The primary bonds include, but are not limited to, covalent bonds, ionic bonds, and hydrogen bonds.

Clean: As used in this disclosure, the term clean refers to an object without dirt, unwanted markings, or undesirable pathogens. When referring to a surface, the term clean can also refer to removing unwanted objects from the surface. The term cleaning refers to the action of making an object clean.

Cleaning Agent: As used in this disclosure, a cleaning agent is a chemical compound used to remove pathogens, dirt, and detritus from a surface.

Cleaning Solution: As used in this disclosure, a cleaning solution is a chemical solution that contains a solvent used to dissolve a cleaning agent.

Combustion: As used in this disclosure, combustion refers to a reduction-oxidation reaction wherein oxygen and a hydrocarbon are combined to release energy, carbon dioxide, and water. In general usage, the meaning of combustion is often extended to describe a reaction between oxygen and a fuel source, such as a hydrocarbon modified by functional groups, which releases energy.

Copolymer: As used in this disclosure, a copolymer is a polymer formed from two or more repeating molecules (also referred to as monomers).

Cosmetic Media: As used in this disclosure, a cosmetic media refers to a chemical substance that is topically applied to a biological organism. The purposes for a cosmetic media include, but are not limited to: a) cleaning the skin and the hair of the biological organism; b) changing the visual, olfactory, and tactile stimuli presented by the biological organism to other nearby biological organisms; and, c) the topical application of a pharmacologically active media.

Covalent Bond: As used in this disclosure, a covalent bond refers to a chemical bond between a first atom and a second atom wherein the first atom and the second atom share each share one or more electrons with each other. This is in contrast to an ionic bond.

Dimer: As used in this disclosure, a dimer refers to the bonding of two or more identical molecules to each other.

Disposable: As used in this disclosure, disposable is an adjective that refers to an object that is designed and intended for a single use. Within this context, an object would be considered disposable if it is not reusable after its initial use.

Essential Oil: As used in this disclosure, an essential oil is a lipid based solution that contains one or more volatile aroma compounds dissolved in a non-polar solvent. Examples of naturally occurring essential oils include, but are not limited to, basil oil, black pepper oil, caraway oil, cannabis flower oil, cedar wood oil, cinnamon oil, citronella oil, chamomile oil, clove oil, davana oil, eucalyptus oil, frankincense oil, horseradish oil, jasmine oil, lavender oil, lemon oil, lemongrass oil, mandarin oil, nutmeg oil, orange oil, oregano oil, peppermint oil, pine oil, sage oil, sandalwood oil, star anise oil, and thyme oil. Basil oil, cedar wood oil, citronella oil, chamomile oil, clove oil, lavender oil, lemongrass oil, and peppermint oil are traditionally considered to have insect repellent and insecticide properties.

Extract: As used in this disclosure, an extract is a solution that contains one or more phytochemicals dissolved in a polar solvent including solvents such as ethanol and water.

Flavonoid: As used in this disclosure, a flavonoid is a phytochemical. The flavonoid comprises a collection of functional groups attached to a chemical backbone selected from the group consisting of: a) the flavone (CAS 525-82-6) chemical group; b) the isoflavone chemical group (CAS 446-72-0); and, c) the neoflavonoid (CAS 51870-64-5) chemical group. Anthocyanins are a common subclass of flavonoid based on the flavone chemical group.

Flow: As used in this disclosure, a flow refers to the passage of a fluid past a fixed point. This definition considers bulk solid materials as capable of flow.

Fluid: As used in this disclosure, a fluid refers to a state of matter wherein the matter is capable of flow and takes the shape of a container it is placed within. The term fluid commonly refers to a liquid or a gas.

Fluid Impermeable: As used in this disclosure, the term fluid impermeable refers to: a) the ability of a structure to not allow a fluid to pass through the structure; or, b) the ability of a material not absorb through the exterior surfaces of the material a fluid that the material is immersed in or exposed to.

Fragrance: As used in this disclosure, a fragrance is a distinctive odor that is generally pleasant.

Gas: As used in this disclosure, a gas refers to a state (phase) of matter that is fluid and that fills the volume of the structure that contains it. Stated differently, the volume of a gas always equals the volume of its container.

Heat Shrink: As used in this disclosure, a heat shrink material is a polymer structure that permanently reduces in volume when exposed to heat. A heat shrink tube is a tubular structure formed from a heat shrink material such that the interior volume of the heat shrink tube will decrease when the heat shrink tube is heated.

Hydrocarbon: As used in this disclosure, a hydrocarbon is a molecule comprising hydrogen and oxygen. Alkanes, alkenes, and alkynes are examples of hydrocarbons.

Hydrogen Bond: As used in this disclosure, a hydrogen bond refers to an electrostatic attraction between: 1) a cation and an anion; 2) a cation and a negative dipole; or, 3) an anion and a positive dipole. The exchange of electrons (as would occur in an ionic bond or covalent bond) does not occur in a hydrogen bond. As a rule, the energy to break an ionic bond is less that the energy required to break a covalent bond or an ionic bond.

Ionic Bond: As used within this disclosure, an ionic bond refers to a chemical bond between a first atom and a second atom wherein the first atom takes an electron from the second atom. This is in contrast to a covalent bond.

Kit: As used in this disclosure, a kit is an assembly of a combination of instruments, equipment, or supplies that are dedicated or intended for use in a specific purpose. Depending on the context, a kit may further include the container within which the instruments, equipment, and supplies are stored.

Lipid: As used in this disclosure, a lipid is an organic molecule that is soluble in nonpolar solvents.

Liquid: As used in this disclosure, a liquid refers to a state (phase) of matter that is fluid and that maintains, for a given pressure, a fixed volume that is independent of the volume of the container.

Monomer: As used in this disclosure, a monomer refers to a molecular structure that bonds to itself in a repeating manner to form a polymer.

Non-Polar Molecule: As used in this disclosure, a non-polar molecule refers to a molecular structure that: a) is electrically neutral; and, b) has a uniform spatial distribution of the electrons within the molecule.

Organic: As used in this disclosure, organic refers to a carbon-based chemical structure. A limited number of carbon-based salts are traditionally considered inorganic chemical structures and are excluded from the study of organic chemistry.

Patient: As used in this disclosure, a patient is a person who is designated to receive a medical treatment, therapy, or service. The term patient may be extended to an animal when used within the context of the animal receiving veterinary treatment or services.

Pharmacologically Active Media: As used in this disclosure, a pharmacologically active media refers to a chemical substance that has a biochemical or physiological effect on a biological organism.

Phase: As used in this disclosure, phase refers to the state of the form of matter. The common states of matter are solid, liquid, gas, and plasma.

Phytochemical: As used in this disclosure, a phytochemical is a pharmacologically active media that is produced in and harvested from a plant. Within this disclosure, a phytochemical comprises a pharmacologically active media containing one or more chemical groups selected from the group consisting of: a) the flavonoid chemical group; b) the terpenoid chemical group (including the carotenoid chemical subgroup of the terpenoid chemical group); c) polyphenol chemical group; d) the polyacetylene chemical group; e) the biological thiol chemical group; and, f) the biological alkaloid chemical group.

Plastic: As used in this disclosure, plastic refers to a manufactured material that is formed from a structure selected from the group consisting of a polymer or a copolymer. Unless stated otherwise, this disclosure assumes that the plastic is formed from organic monomers.

Polar Molecule: As used in this disclosure, a polar molecule refers to a molecular structure that: a) is electrically neutral; but, b) does not have a uniform spatial distribution of the electrons within the molecule. A polar molecule will present one or more electrically positive poles and the same number of electrically negative poles within the molecular structure.

Polarity: As used in this disclosure, the term polarity is used to describe a physical property or physical characteristic wherein: 1) the physical property or physical characteristic manifests two opposing attributes, tendencies, characteristics, or principals; and, 2) the two opposing attributes, tendencies, characteristics, or principals have an intrinsic separation, alignment, or orientation.

Polyacetylene: As used in this disclosure, a polyacetylene is a phytochemical. The polyacetylene comprises a collection of functional groups attached to a chemical backbone that is formed from, or contains, one or more chains built from the $(C_2H_2)_n$ polymer where $n>=2$.

Polymer: As used in this disclosure, a polymer refers to a molecular chain that comprises multiple repeating units known as monomers. The repeating unit may be an atom or a molecular structure.

Polyphenol: As used in this disclosure, a polyphenol is a phytochemical. The polyphenol comprises a collection of functional groups attached to a chemical backbone formed from two or more phenol (CAS 108-95-2) molecules. A lignan refers to a dimer containing two or more identical molecules that contain a phenol.

Protected Space: As used in this disclosure, a protected space is a negative space within which an object is stored. The protected space is enclosed by a barrier structure that: a) prevents damage to the object contained within the protected space; b) maintains an environment suitable within the protected space that is appropriate for the object; or, c) protects the object within the protected space from potential dangers that are outside of the protected space.

Reduction-Oxidation Reaction: As used in this disclosure, a reduction-oxidation reaction (also known as a redox reaction) is a chemical reaction involving the transfer of electrons between the reactants of the reaction.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Shrink Wrap: As used in this disclosure, a heat shrink material is a polymer sheeting that permanently reduces in volume when exposed to heat. Shrink wrap is used to create a protected space for a product that is being stored.

Solid: As used in this disclosure, a solid refers to a state (phase) of matter that: 1) has a fixed volume; and, 2) does not flow.

Solution: As used in this disclosure, a solution is a uniform mixture of two or more compounds in a liquid phase. The major component selected from the two or more compounds that forms the solution is called the solvent. The components remaining in the two or more compounds are called the solute. A polar solvent is a solvent formed from polar molecules. A non-polar solvent is a solvent formed from non-polar molecules. The rule of thumb that "like dissolves like" states that: a) solutes formed from polar molecules will dissolve in polar solvents but will not dissolve in non-polar solvents; and, b) solutes formed from non-polar molecules will dissolve in non-polar solvents but will not dissolve in polar solvents.

Surfactant: As used in this disclosure, a surfactant is a substance that decreases the surface tension of a fluid. Within water, a surfactant often comprises polar and non-polar functional groups for the purpose of improving the solubility of otherwise non-soluble substances in water.

Terpenoid: As used in this disclosure, a terpenoid is a phytochemical. The terpenoid comprises a collection of functional groups attached to a chemical backbone of a terpene. The terpene is a chemical structure formed from an integer number of isoprene (CAS 78-79-5) molecules. The functional groups attached to the terpenoid will always include at least one hydroxyl (alcohol) group.

Therapeutic: As used in this disclosure, therapeutic is an adjective that refers to a medical, ameliorative, or hygienic substance, process, procedure, or device.

Thiol: As used in this disclosure, a thiol is a functional group formed with hydrosulfide (also known as bisulfide). The thiol has an ionic chemical formula HS(—). As a functional group, the thiol has the chemical formula of RSH.

Topical: As used in this disclosure, topical is an adjective that is associated with a media selected from the group consisting of a pharmacologically active media and a cosmetic media. Topical indicates that the pharmacologically active media is applied directly to the skin.

Towel: As used in this disclosure, a towel refers to an absorbent sheeting material that is used to remove liquid from an object. A towel formed from an absorbent paper sheeting is called a paper towel.

Virus: As used in this disclosure, a virus is a biological entity that is capable of reproduction but does not have the biological mechanisms to generate the energy for replication. A virus "infects" a host cell and uses the biochemical biological processes of the host cell as the energy source that allows the virus to replicate. Because the virus is incapable of independently generating the biochemical energy necessary for reproduction, the traditional view is that viruses are not a form of life. All viruses comprise a nucleic acid structure and a protein shell. The nucleic acid structure is genetic material that is selected from the group consisting of RNA and DNA. The nucleic acid structure is enclosed within the protein shell. The protein shell is known as the capsid. The proteins of the capsid are encoded by the nucleic acid structure. The capsid: a) protects the nucleic acid structure when the virus is dormant; and, b) attaches the virus to a biological structure of a host cell that is suitable to support the replication of the virus. More evolved viruses further comprise an envelope. The envelope is a lipid based structure that is similar to a cell membrane. By similar to the cell membrane is meant that: a) the envelope is formed with a bilayer lipid structure similar to a cell membrane; and, b) the envelope will display membrane protein structures to its environment in a manner similar to a cell membrane. The envelope encloses the capsid and the nucleic acid structure. In this disclosure, a virus formed with an envelope is referred to as an evolved virus. The term virus can refer to viruses with or without an envelope.

Volatile: As used in this disclosure, volatile refers to a substance that will evaporate or sublimate into a gas state at normal temperature and pressure.

Volatile Organic Compounds: As used in this disclosure, a volatile organic compounds refers to an organic compounds with a relatively low boiling point such that a significant portion of the volatile organic compounds will exist as a gas at normal temperature and pressure. Volatile organic compounds is commonly abbreviated VOC. When measuring volatile organic compounds within the atmosphere, commercially available sensors will generally measure and report all volatile organic compounds as a single aggregated measurement referred to as the total volatile organic compounds. Total volatile organic compounds is commonly abbreviated TVOC.

Wax: As used in this disclosure, a wax can be any of numerous substances of plant, animal, or synthetic origin composed principally of nonpolar organic compounds of high molecular weight including, but not limited to, mixtures of saturated or unsaturated hydrocarbons, and lipids including esters of long chain alcohols or fatty acids. Waxes are solid at room temperature and insoluble in water. For the purpose of this disclosure, a wax is considered to be a lipid.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention 8 is to be limited only by the scope of the following claims and their equivalents.

What is claimed is:

1. A disposable personal towel cleaning kit comprising a cleaning towel and a cosmetic media towel;
   wherein the disposable personal towel cleaning kit is adapted for use with a patient;
   wherein the cleaning towel is adapted for use in applying a cleaning solution to the skin of the patient;
   wherein the cosmetic media towel is adapted for use in applying a cosmetic media solution to the skin of the patient;
   wherein the cleaning towel comprises a first textile sheeting, a cleaning solution, and a first shrink wrap;
   wherein the first textile sheeting absorbs and stores the cleaning solution;
   wherein the first shrink wrap forms a fluid impermeable protected space around the first textile sheeting and the cleaning solution;
   wherein the cosmetic media towel comprises a second textile sheeting, a cosmetic media solution, and a second shrink wrap;
   wherein the second textile sheeting absorbs and stores the cosmetic media solution;
   wherein the second shrink wrap is a shrink wrap used to enclose the second textile sheeting and the cosmetic media solution.

2. The disposable personal towel cleaning kit according to claim 1
   wherein the disposable personal towel cleaning kit is a therapeutic apparatus;
   wherein the cleaning towel is intended for a single use;
   wherein the cosmetic media towel is intended for a single use;
   wherein the cleaning towel is disposable;
   wherein the cosmetic media towel is disposable.

3. The disposable personal towel cleaning kit according to claim 2
   wherein the cleaning towel is a sheeting structure;
   wherein the cleaning towel is a flexible structure;
   wherein the cleaning towel is a textile based structure;
   wherein the cleaning towel is an absorbent structure.

4. The disposable personal towel cleaning kit according to claim 3
   wherein the cosmetic media towel is a sheeting structure;
   wherein the cosmetic media towel is a flexible structure;
   wherein the cosmetic media towel is a textile based structure;
   wherein the cosmetic media towel is an absorbent structure.

5. The disposable personal towel cleaning kit according to claim 4
   wherein the first textile sheeting is a sheeting structure;
   wherein the first textile sheeting is a flexible structure;
   wherein the first textile sheeting is a textile based structure;
   wherein the first textile sheeting is an absorbent structure;
   wherein the first textile sheeting is a disposable structure.

6. The disposable personal towel cleaning kit according to claim 5
   wherein the second textile sheeting is a sheeting structure;
   wherein the second textile sheeting is a flexible structure;
   wherein the second textile sheeting is a textile based structure;
   wherein the second textile sheeting is an absorbent structure;
   wherein the second textile sheeting is a disposable structure.

7. The disposable personal towel cleaning kit according to claim 6 wherein the cleaning solution is a liquid phase chemical;
   wherein the cleaning solution is a phytochemical;
   wherein the cleaning solution is a surfactant;
   wherein the cleaning solution removes polar and nonpolar molecular structures that are on the skin of the patient;
   wherein the cleaning solution dissolves polar and nonpolar molecular structures that are on the skin of the patient.

8. The disposable personal towel cleaning kit according to claim 7
  wherein the cosmetic media solution is a liquid phase chemical;
  wherein the cosmetic media solution is a phytochemical;
  wherein the cosmetic media solution is a pharmacologically active media;
  wherein the cosmetic media solution provides a therapeutic benefit to the skin of the patient;
  wherein the cosmetic media solution is topically applied to the skin of the patient.

9. The disposable personal towel cleaning kit according to claim 8
  wherein the first shrink wrap is a plastic structure;
  wherein the first shrink wrap is a fluid impermeable structure;
  wherein the first shrink wrap is a disposable structure that is intended for a single use;
  wherein the first shrink wrap is a shrink wrap used to enclose the first textile sheeting and the cleaning solution.

10. The disposable personal towel cleaning kit according to claim 9
  wherein the second shrink wrap is a plastic structure;
  wherein the second shrink wrap is a fluid impermeable structure;
  wherein the second shrink wrap forms a fluid impermeable protected space around the second textile sheeting and the cosmetic media solution;
  wherein the second shrink wrap is formed from a heat shrink material.

11. The disposable personal towel cleaning kit according to claim 10
  wherein the first shrink wrap is formed from a heat shrink material;
  wherein the first shrink wrap is heated to wrap tightly around the first textile sheeting and the cleaning solution.

12. The disposable personal towel cleaning kit according to claim 11
  wherein the second shrink wrap is heated to wrap tightly around the second textile sheeting and the cosmetic media solution;
  wherein the tight fit second shrink wrap inhibits the evaporation of the cosmetic media solution from the second textile sheeting while the cosmetic media towel is in storage.

* * * * *